United States Patent [19]

Beu

[11] 4,305,708
[45] Dec. 15, 1981

[54] DENTAL ARTICULATOR

[75] Inventor: Richard A. Beu, Eggertsville, N.Y.

[73] Assignee: Teledyne Hanau, a division of Teledyne, Inc., Buffalo, N.Y.

[21] Appl. No.: 2,190

[22] Filed: Jan. 9, 1979

[51] Int. Cl.³ .......................................... A61C 11/00
[52] U.S. Cl. ...................................... 433/57; 433/66
[58] Field of Search ................. 32/32; 433/57, 61, 66, 433/64

[56] References Cited

U.S. PATENT DOCUMENTS

| | | | |
|---|---|---|---|
| 3,590,487 | 9/1968 | Guichet | 32/32 |
| 3,818,595 | 6/1974 | Stuart | 32/32 |
| 3,905,112 | 9/1975 | Swanson | 32/32 |
| 4,024,640 | 5/1977 | Guichet | 32/32 |
| 4,034,475 | 7/1977 | Lee | 32/32 |
| 4,209,909 | 7/1980 | Lee | 433/57 |

FOREIGN PATENT DOCUMENTS 7900038 2/1979 World Intel. Prop. Org. ........ 32/32

Primary Examiner—Gene Mancene
Assistant Examiner—John J. Wilson
Attorney, Agent, or Firm—Raymond F. Kramer

[57] ABSTRACT

A dental articulator for simulating relative jaw and tooth movements, especially useful for producing centric, lateral and forward relative jaw movements of simulated jaws containing a patient's simulated tooth structure, includes a plurality of selectable, pre-set, positive positions for locating simulated condyles and condylar joints to match those of a patient, shaft means mounted on the condyles, adjustable means for simulating superior, posterior and medial walls of condylar joints and override means to maintain the simulated jaws and teeth in relatively movable centric position when engaging the shaft and allowing accurate simulated forward and sideward relative jaw movements when disengaged therefrom. Also disclosed are preferred means for mounting the condyles and condylar joint wall parts and wall parts of improved structure to promote accurate simulation of actual condylar movements.

14 Claims, 13 Drawing Figures

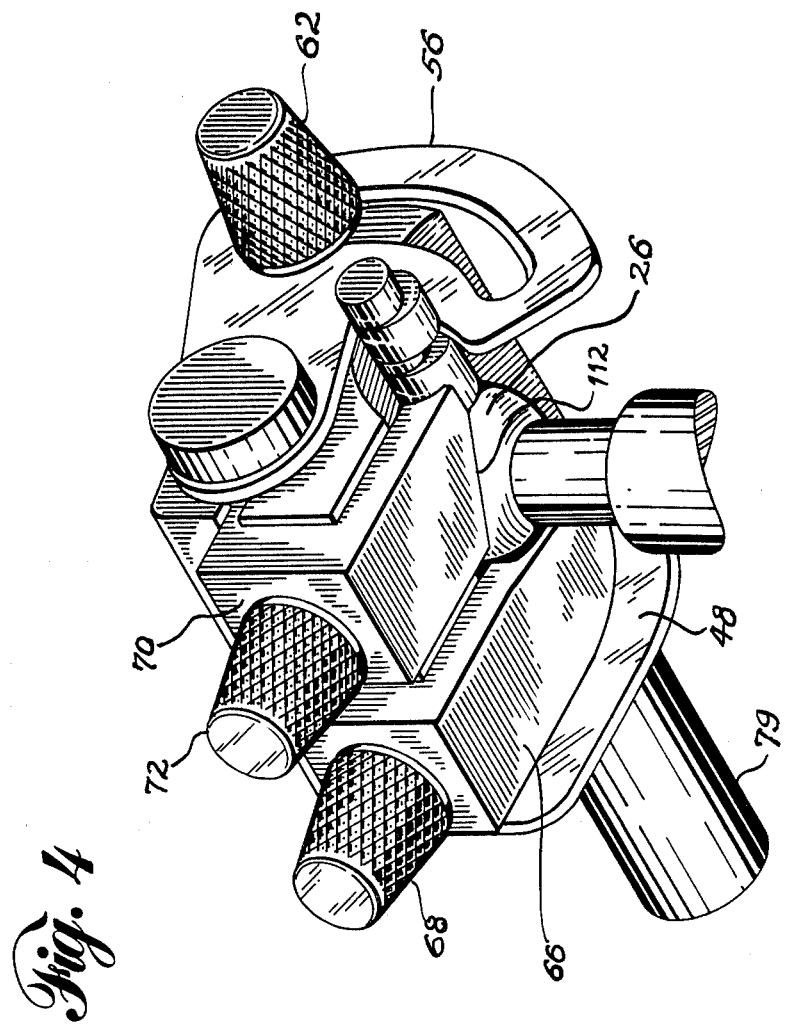

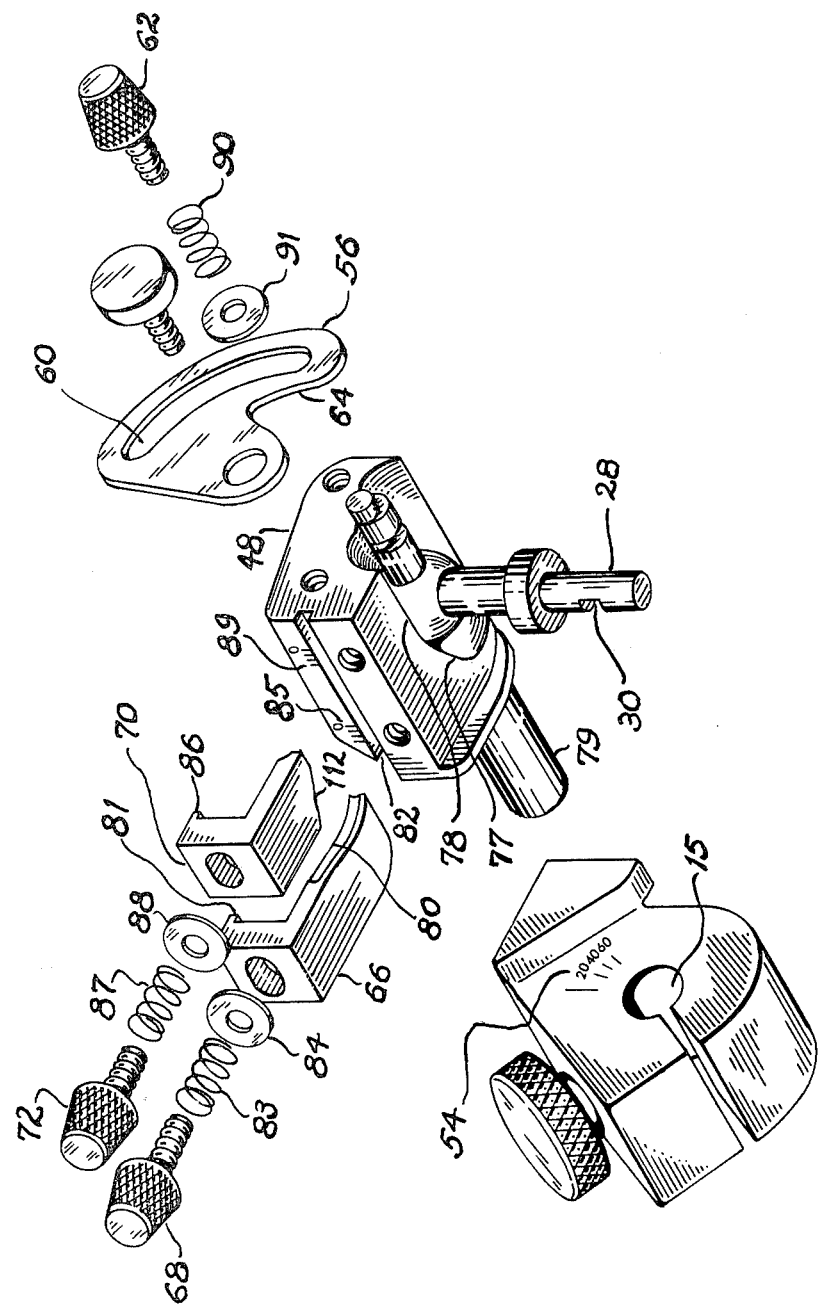

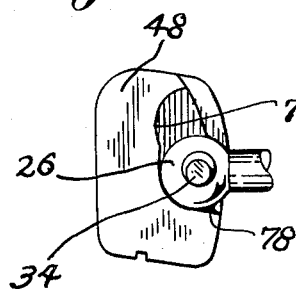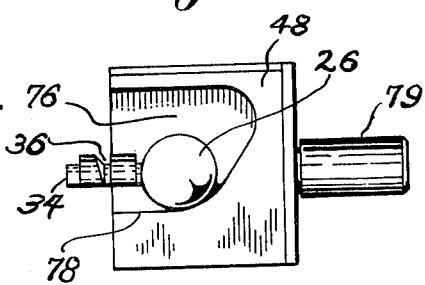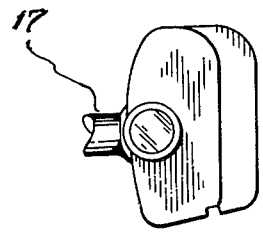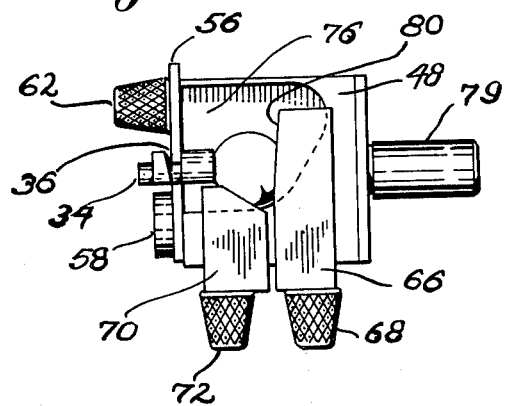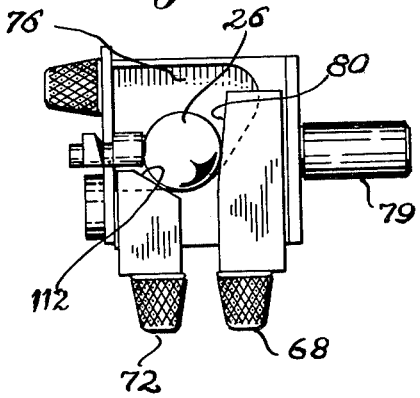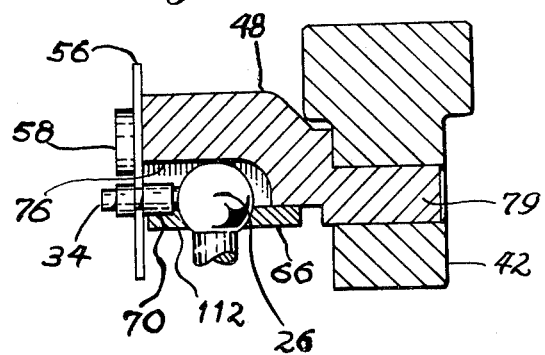

DENTAL ARTICULATOR

This invention relates to dental articulators. More particularly, it relates to such articulators which simulate a dental patient's mandibular movements by creation of simulated condyles and condylar joints.

As is well known in the art, dental articulators are useful to dentists, dental laboratory technicians and dental educators. They have been employed in the construction of removable and fixed prostheses and are especially useful in allowing the dentist and dental technician to shape such prostheses so that they fit and function satisfactorily. In such prostheses the maxillae and mandibles are relatively movable in simulation of normal jaw movements without making objectionable contacts and without obstructing free movements.

Although the dental articulator art is a comparatively old one, in recent years patents have been granted on various improved articulators, many of which are designed to simulate better actual jaw movements of a patient. Among such patents there may be mentioned U.S. Pat. No. 3,897,632, granted to Richard A. Beu, of which the present invention may be considered to be an improvement, and U.S. Pat. No. 3,206,852 (Swanson). Other patents which may be considered as relevant to some degree to the present invention include U.S. Pat. Nos. 2,237,050 and 3,905,112, both of which relate to centric locks, 3,224,096, which relates to condyle spacing; 3,769,708, which is relevant to medial wall replacement; and 2,245,397, 3,343,264, 3,350,782, 3,590,487, 3,896,550 and 4,024,640, all of which illustrate side shift. The meanings of such terms either are well known in the art or will be apparent from the description in the present specification.

Although the prior art patents referred to, which are those known to the present applicant and found in a search of classified patents, principally conducted in class 32, subclass 32, describe apparatuses for simulating condylar and mandibular movements, the present invention is for a simplified and improved articulator which can be employed more easily and which provides a more accurate simulation of such movements.

In accordance with the present invention there is provided in a dental articulator for simulating relative jaw and tooth movements, an improvement which comprises a pair of simulated condyles axially spaced apart on a lower mounting means which simulates a part of a lower jaw, a pair of shafts extending sidewardly and outwardly from the condyles, each of which shafts includes at least a partial peripheral guide, a pair of movable mounting means for a simulated maxilla for movement thereof with respect to the condyles, each of said mounting means being spaced apart so as to support means for simulating condylar joint walls, superior and medial wall means held to each of the mounting means for the simulated maxilla at each of the simulated condyles, and bearable against the condyles, said superior and medial wall means being movable to desired positions to simulate condylar joint walls and to control condylar movements, and override means adjacent to each of the condyles, for selectively bearing against a portion of each of the shafts extending from such condyles to hold the articulator in movable centric position, and for disengaging from such shafts to permit simulated forward and sideward jaw movements, which override means are rotatable with respect to the peripheral guides of the shafts to hold the simulated maxilla against lateral movement when in centric position and are disengageable from said guides to allow removal of the superior and medial condylar joint wall means, mounting means and simulated maxilla from the shafts and the condyles in such disengaged position. In preferred aspects of the invention the condyles are each spherical (at least for all the surfaces thereof which contact condylar joint walls or guidances), the simulated condyles are each selectively, positively and accurately spaceable apart in any of at least three pre-set positions on the lower mounting means, the pair of shafts extending from the condyles are matching shafts including channel or groove structure, such as a peripheral channel or annular groove, and posterior wall means are present and are held to each of the mounting means for the simulated maxilla at each of the simulated condyles, are bearable aginst the condyles and are movable to desired position to simulate parts of condylar joint walls and to control condylar movements, the condylar wall parts are vertically rotatably adjustable (for the superior wall portion) and laterally adjustable (for the posterior and medial wall parts), a part of the superior wall part is vertically curved to produce a smooth transitional movement of the condyle with respect to the condylar wall as the condyle moves from bearing against the posterior or vertically curved portion of the superior wall to bearing against the medial wall, while still bearing against the upper portion of the superior wall, and the override means or centric guide means is holdable in a peripheral channel or annular groove in the shaft on the condyle, includes an arc-shaped guide means and is removable from the condyles with other portions of the upper articulator framework, when in disengaged position. Also, preferably from 4 to 6 mounting positions are available for each condyle sphere, the condylar distances between adjacent positions is from 1 to 1.6 cm. (twice those between adjacent openings) and the condylar joint wall means positions are similar in number and spacing. Other aspects of the invention considered to be of importance are the curving of the posterior portion of the superior condyle wall part so that condyle movement along it is continuous with such movement along the medial wall part and the transition between them is curved and gradual. Additionally, it is considered important that the centric lock or override means is adjacent to the means for adjusting positions of the condyle wall parts, which facilitates use of the articulator.

Among specific structural aspects of this invention important to the success of the articulator are the centric latching mechanisms which are pivotally attached to the condylar guidance keystone or mount on the upper articulator frame or member. Such latch or override member, when engaged, restricts the upper member to an accurate opening and closing hinge movement about the two condylar elements of the lower frame or member, which movement is devoid of any lateral or translational components. The plurality of mounting holes, laterally spaced in the upper and lower members or frames, permits the spacing of the condylar guidances and condylar elements, matching such spacings exactly between such guidances and elements (walls and spheres,) and sufficiently satisfactorily simulates the patient's condyle spacing. The laterally adjustable medial and posterior walls are other important aspects of the present invention, especially taken in conjunction with the rotatably adjustable superior wall and the cooperative shapes of the superior, posterior and medial walls, which guide the condylar elements.

Various other structures and advantages of the present invention will be described and the invention will be readily understood by reference to this specification and the description herein, taken in conjunction with the drawing in which:

FIG. 4 is a perspective view of the under side of a right side condylar guidance assembly;

FIG. 5 is a disassembled perspective view of the under side of the right condylar guidance assembly of FIG. 4;

FIG. 6 is a fragmentary elevational view of the simulated condylar joint of FIGS. 1–5;

FIG. 7 is a fragmentary bottom plan view of such joint, omitting the mount for the condyle;

FIG. 8 is another side elevational view of the condylar joint assembly;

FIG. 9 is a bottom plan view of the condylar guidance assembly of FIGS. 6–8, with adjustments in closed position;

FIG. 10 is a bottom plan view of the condylar guidance assembly with adjustments in open position;

FIG. 11 is a sectional elevational view of the condylar guidance assembly of FIGS. 1–8;

Figure 1:
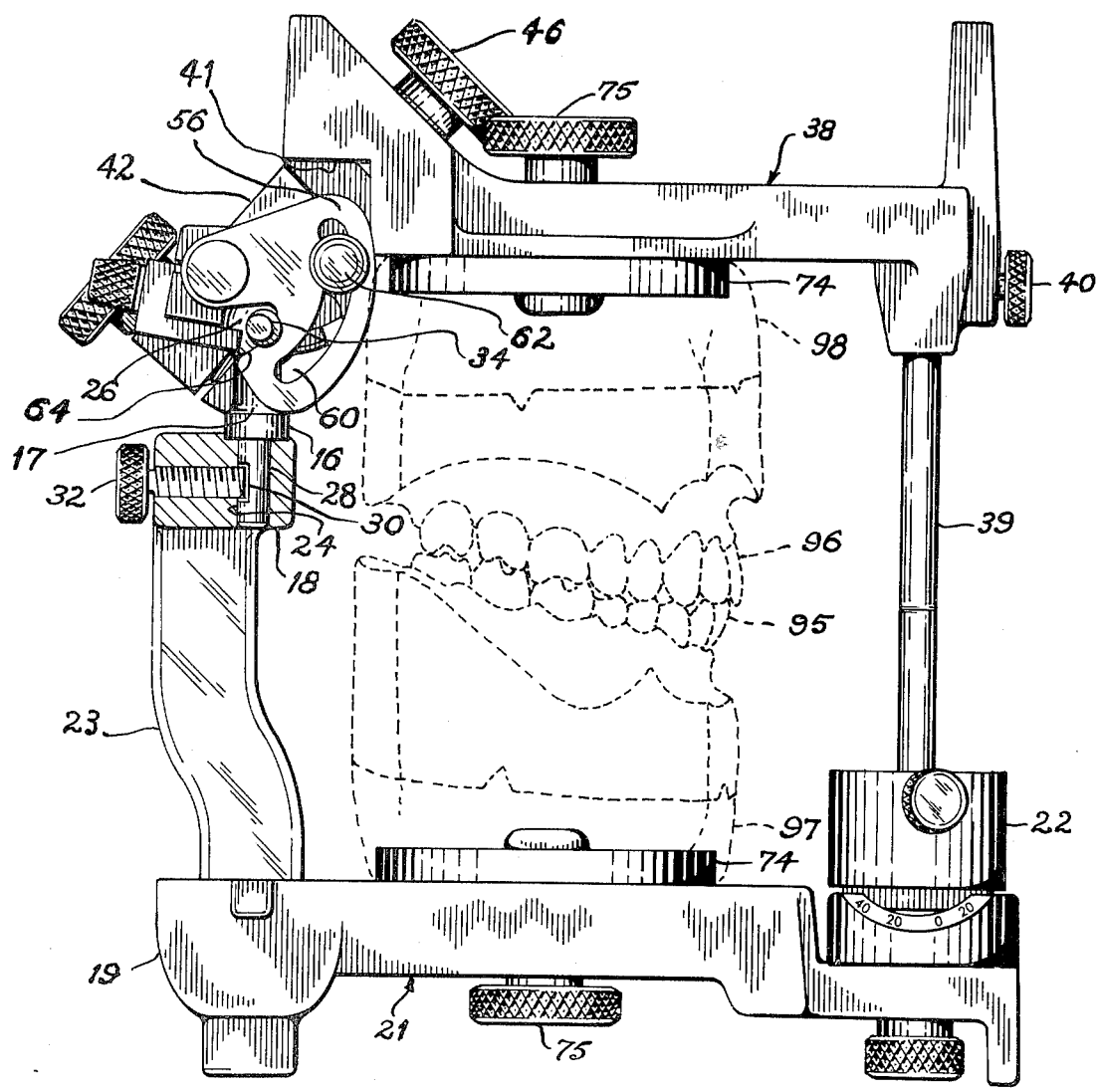
FIG. 1 is a partially sectioned right side elevational view of one form of an articulator of this invention, with simulated teeth and jaw parts, shown in phantom, positioned therein.
Figure 2:
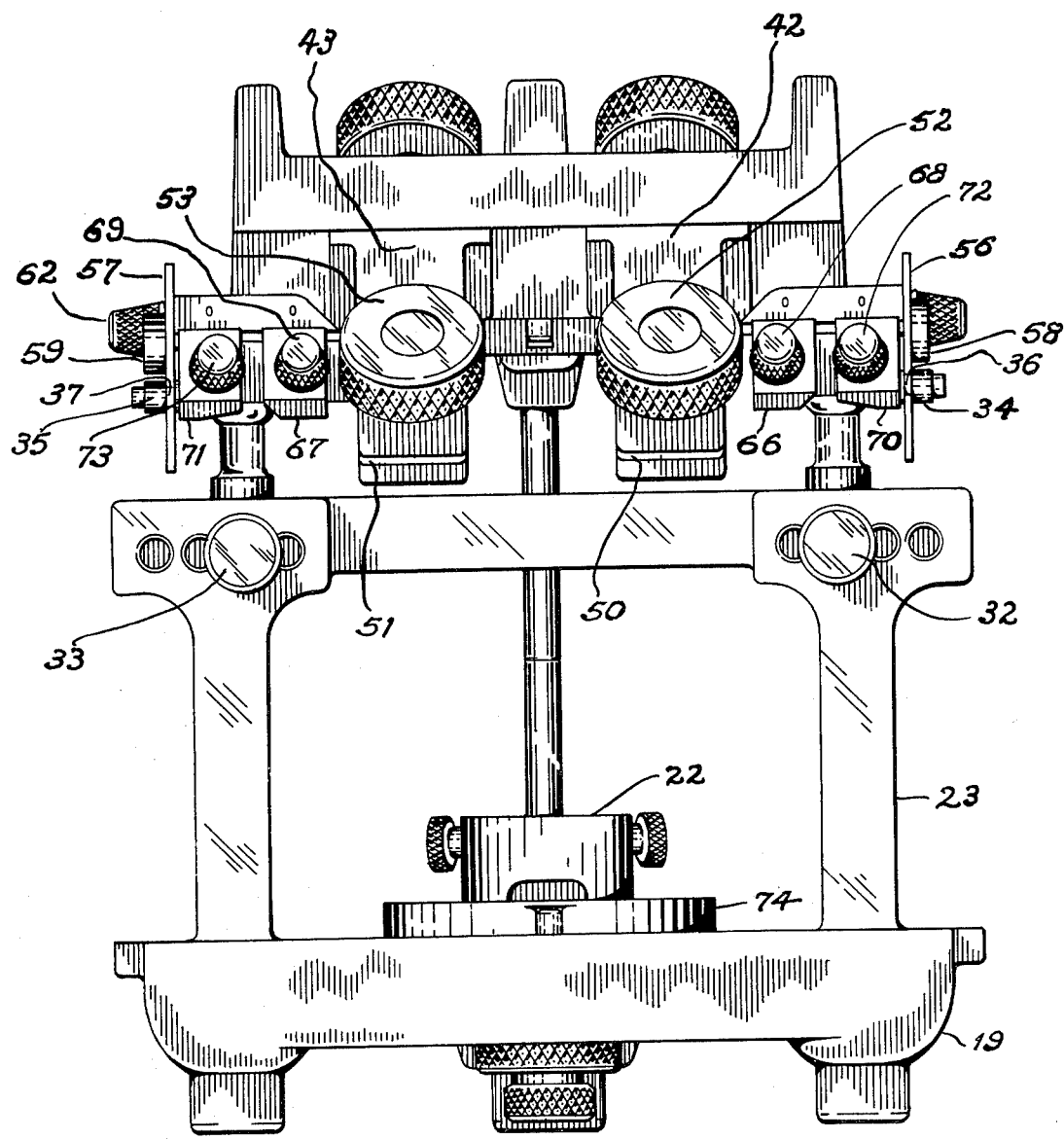
FIG. 2 is a rear elevational view of such articulator.
Figure 3:
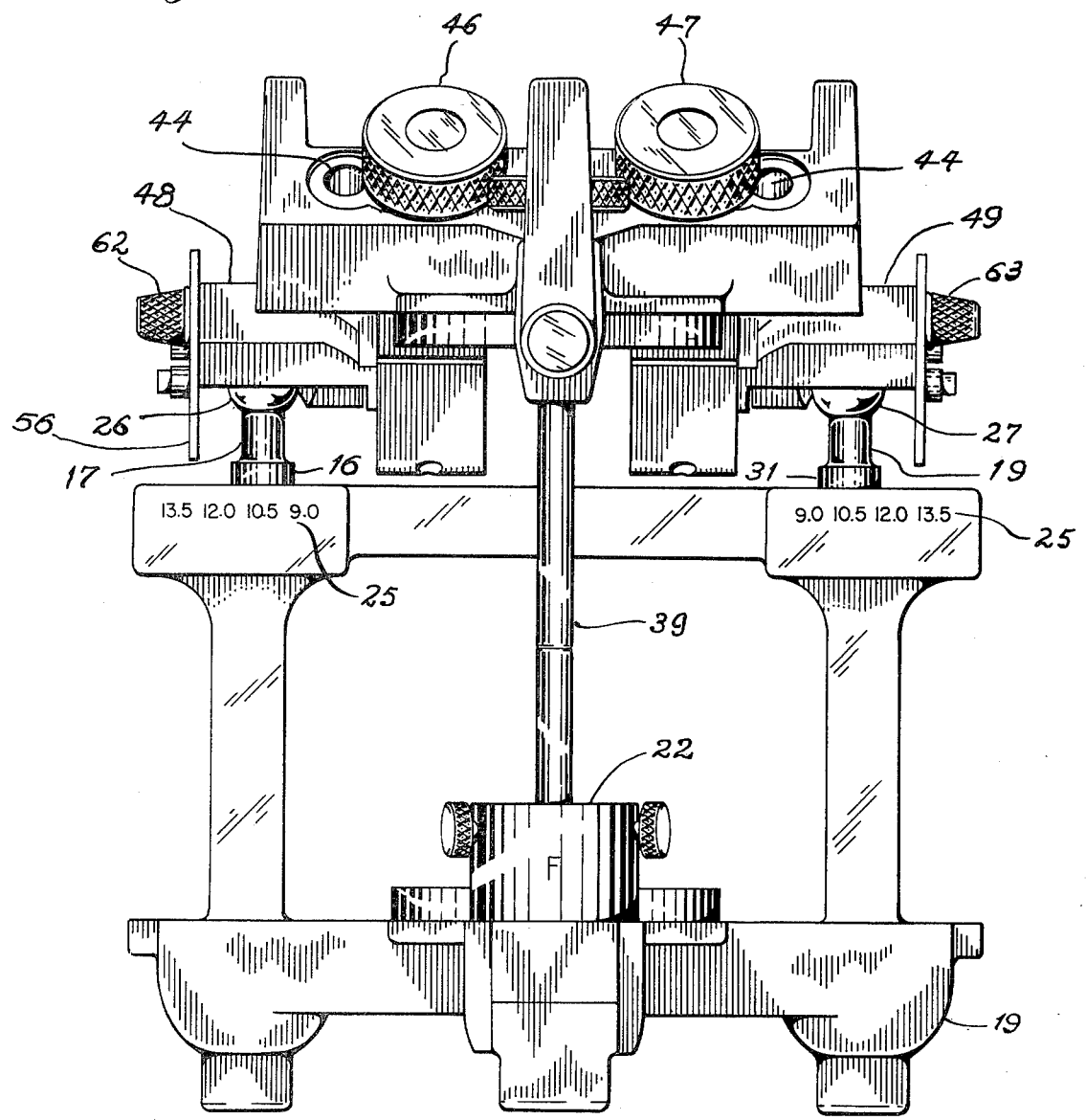
FIG. 3 is front elevational view thereof.

In FIGS. 1–3 there is illustrated a preferred embodiment of the present improved Arcon type articulator. This articulator includes a T-shaped lower member or frame part 21, to which there is affixed at a forward end thereof an incisal cup 22. (In this description the front portion of the articulator is that corresponding to the fronts of the jaws simulated thereby and to the incisors of the teeth mounted therein). A generally vertical or upwardly extending bridge member or part 23 is held in position in wells 19, located at the rear portion of the lower member, by screws, not shown. Eight holes, each designated by the numeral 24, four on each side of the mid-sagittal plane and in a line parallel to the transverse axis of the articulator, pass vertically through upper portions 18 of the bridge member and numerals 25, indicating the metric spacing, in centimeters, between such paired or matching holes, appear on frontal portions thereof. The measurements given are condyle spacings between condyles mounted in symmetrically corresponding holes. Spherical condylar elements 26 and 27, also referred to as simulated condyles, are joined to and supported by vertical cylindrical rod members 17 and 19, having enlarged collar portions 16 and 31. The rods are of reduced diameter, as shown at numeral 28 (see FIG. 5) for entry into the selected holes 24 in the bridge member. The means for determining in which holes 24 the condyles will be mounted is an accessory known in the art as a facebow, a caliper-like device with calibrated rods for application to a patient and to an articulator. Such will be referred to in more detail later. Flat portions 30, located on the condyle mounts, are engaged by flat ends of thumbscrews 32 and 33 to fix the condyles in position and to assure repeated accurate positioning of the condylar elements. Diametrically opposite to each other and parallel to the transverse axis through the holes 24 and the condyle spheres are shafts, studs or rods 34 and 35, which are set into the condylar elements. Each of said shafts contains an annular or peripheral groove, designated 36 and 37. The shafts include end portions of reduced diameters so that they may fit and support the facebow mentioned previously. The lower member assembly thus described, including the base, bridge member, mounting for the condyles and the condyle-shaft combinations, simulates a patient's mandible.

The forward end of the T-shaped upper member 38 includes an incisal pin 39 which is vertically adjustable and fixable in place by means of a thumbscrew 40. Such incisal pin is capable of maintaining a vertical support at this frontal section in cooperation with incisal cup 22. At the rear and bottom of the upper member is a laterally disposed keyway 41 which is capable of accepting and fitting together with keystones 42 and 43. Eight holes 44, four on each side of the mid-sagittal plane and in a line parallel to the transverse axis, angularly enter at the top of the upper member and intersect the interior corner of keyway 41 at their exits. Such holes are identified by numerals to indicate their matching relationship or equivalence with holes 24 and numerals 25 of bridge member 23.

Keystones 42 and 43 have keyed sections which fit to and may be slid into position with respect to keyway 41 of the upper member. Threaded holes (not shown), angularly placed in the keyed sections, cooperate with holes 44 and accept threaded thumbscrews 46 and 47, which rigidly secure the keystones to the upper member at a hole setting compatible with the previous selection of such setting on the lower member. In the outer sides of the keystones are diametrical bearing holes 15, which accept shaft 79 of condylar guidance member 48 and that (not shown) of member 49. Parallel to and cutting into the bearing holes from the rear of the keystones are slots 50 and 51, which allow for provision of a collet-like constraint on the shafts of the condylar guidances when thumb screws 52 and 53 are tightened. Angular graduations 54 at the outer side of the keystone provide a direct reading of the angular extent of rotation of the condylar guidance members with respect to a horizontal plane. Such condylar guidances include a plurality of elements which together form curved bearing surfaces to engage condylar elements 26 and 27 and to simulate the walls of a condylar joint. (It will be understood that when in this description reference is made to one condyle, one condylar guidance or any other one of a matched pair of items, such description also applies to the other of such pair or multiplicity but for the sake of brevity such description is not repeated herein).

When the articulator is at centric position, a position from which all movements thereof may be considered to originate, the condylar elements 26 and 27 are in their most retruded and superior positions with respect to the bearing surfaces of the condylar guidance, devoid of any lateral translation. This centric position may be locked in by engaging the centric latches or override mechanisms 56 and 57. Such centric latches rotate about the axles 58 and 59 while arcuate slots 60 track about thumb screws 62 and 63. Arcs of engagement at 64 emanate from center points adjacent to axles 58 and 59, respectively. This causes the centric latch to enter the annular grooves 36 and 37 of studs 34 and 35, progressively forcing the condylar elements 26 and 27 into their centric positions. The centric latches or overrides are retained in this centric relationship by tightening of thumbscrews 62 and 63. Similarly, by loosening such thumbscrews the centric latches may be rotated and disengaged, permitting forward and sideward movements of the simulated maxilla and also allowing removal of the maxillary portion of the articulator when such may be desired.

The adjustable medial walls 66 and 67 slide laterally, forming angular guidance surfaces for the condylar elements 26 and 27. Such walls may be locked in their adjusted positions by thumbscrews 68 and 69. Similarly, adjustable posterior walls 70 and 71 also slide laterally, form adjustable posterior guidance surfaces for the condylar elements and may be locked in their adjusted positions by thumbscrews 72 and 73. The upper member assembly, as indicated, is regarded as the patient's maxilla and the adjustably attached condylar guidances simulate the glenoid fossae.

Mounting plates 74 are replaceably affixed to lower member 21 and upper member 38 by captive thumbscrews 75. Such plates hold models depicting the patient's mandibular and maxillary tooth structures 95 and 96 in centric relationship in cooperation with intermediate settable material, such as a gypsum plaster or other suitable substitute, 97 and 98.

Detailed illustrations of the condylar guidance assembly are given in FIGS. 4–11. In FIG. 4 condylar element or condyle 26 is at rest at its zero centric position, a point from which all simulated relative movement of the mandible (lower member 21) is made. Condylar guidance or joint wall member 48 is the principal determinant of the novel relative mandibular movements of the present articulator. The superior surface 76 thereof is contoured with a protrusive convexity to simulate an average anatomical curvature of the glenoid fossae.

The medial surface 77 is also curved to simulate the average medial wall of the patient's glenoid fossae. The curved medial surface 77 is a cooperative extension of the curved substantially vertical posterior wall of the superior surface 76. When condylar element 26 rests against superior surface 76 and the straight posterior surface 78 it is said to be at the centric position. The center of condylar element 26 at this centric position is on the same center line as shaft 79. Shaft 79 enters keystone 42 and permits the condylar guidance assembly to be adjustably rotated to the same protrusive angulation as the patient. Calibration 54 appears on the vertical wall of keystone adjacent to shaft 79 and provides a reference for the angulation of protrusion. Thus, the superior surface or condylar wall portion is adjustably rotatable, as are the associated medial and posterior walls.

An adjustable medial wall 66 is laterally slidable and positionable from the centric position. It allows condylar element 26 to be guided by the curved medial wall at 77 prior to following a 4° to 8°, preferably 6° average guidance angle at 80. The transition to this guidance angle is curved to match the contour of the superior surface 76 and is concave and of essentially the same radius as the condylar element 26. This forces condylar element 26 to remain in contact with the superior surface 76 when following guidance angle 80 during a lateral movement from centric position. The adjustable medial wall 66 is guided by its key at 81 in cooperation with lateral keyway 82 in condylar guidance 48. Such medial wall is adjustably fixable in place by thumbscrew 68. When loosening thumbscrew 68, spring 83 exerts a constant pressure against washer 84 to prevent accidental movement of the medial wall adjustment before again tightening thumbscrew 68.

Calibration 85 appears on condylar guidance 48 adjacent to keyway 82. When an indicating line on the adjustable medial wall 66 aligns with the 0 of calibration 85 guidance angle 80 will be considered at centric and in such position there is no medial surface 77 influence on condyle 26 during lateral motions. When set at the fourth line of calibration 85 a three millimeter lateral movement of condylar element 26 with respect to curved medial surface 77 is allowed before guidance angle member 80 is engaged.

Adjustable posterior wall 70 is also laterally slidable from centric position. It has a fully extending angled guiding surface, the end of which intersects the posterior surface 78. It is also concave and of the same radius as condylar element 26, which forces the condylar element to remain in contact with the superior surface 76 while following the adjustable posterior wall from a centric position. The adjustable posterior wall 70 is guided by its key 86, which may be slid in lateral keyway 82. This adjustable posterior wall may be fixed in place by thumbscrew 72. When thumbscrew 72 is loosened spring 87 exerts a constant pressure against washer 88 to secure the adjusted posterior wall against accidental movement before tightening of the thumbscrew.

A calibration 89 appears adjacent to the aforementioned calibration 85. An indicating line on adjustable posterior wall 70 is aligned with the 0 of calibration 89. When adjusted thusly, upon a lateral movement there is allowed a 3 millimeter lateral guidance of the condylar element 26 along the posterior surface 78 before the guidance surface 112 is engaged. When set at the fourth line of calibration 89 the adjustable posterior wall 70 and its guiding surface 112 are at centric position and condylar element 26, upon a lateral movement, will immediately follow the guiding surface 112 without influence of posterior surface 78. Of course, because condylar element 26 is fixed in position in the present articulator, as opposed to the situation in the patient,, wherein it is movable, it may be more accurate to state that the guiding surface follows the condylar element.

Shaft or stud 34 extends from the center of condylar element 26, which element is selectively, positively and accurately positionable and spaced apart from a similar condylar element or condyle, being held to bridge member 23. Stud 34 is coaxial with a cooperating stud on the left side of the articulator. It contains a partial peripheral guide, shown here as an annular groove 36, for the engagement of centric latch 56. Centric latch 56 rotates about its axle 58 and arcuate slot 60 therein tracks over thumb screw 62. The center of the arc of engagement 64 is adjacent to the center of axle 58 and allows a progressive entry of the centric latch 56 into annular groove 36 and against the walls thereof. This, in turn, forces condylar element 26 against posterior surface 78 and superior surface 76. It is noted that when the arcuate engagement means 64 enters annular groove 36 it prevents a lateral shifting of upper member 38 relative to lower member 21 because the width of the centric latch or override mechanism 56 is essentially the same as (or approaches) that of annular groove 36. A chamfer at the outside edge of annular groove 36 assists the centric latch 56 in entering the groove, even though the two engaging portions are not initially in exact alignment. Centric latch 56 may be locked in position by thumbscrew 62. When such thumbscrew is loosened spring 90 exerts a constant pressure against washer 91 to prevent the latch from pivoting uncontrollably. With the latch engaged, condylar element 26 is locked in centric position, it being in the most retruded and superior position in the condylar guidance 48, without any lateral movement being possible.

Figure 12:
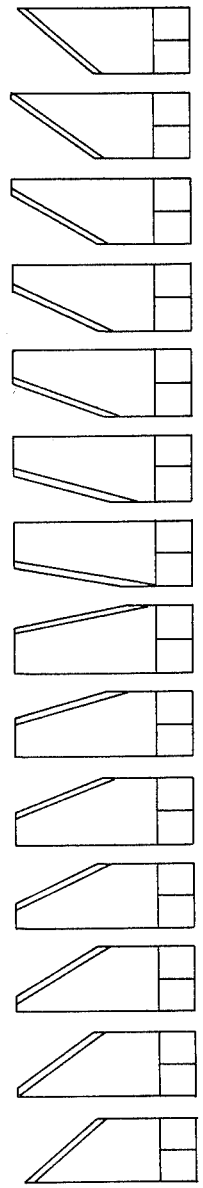
FIG. 12 is a top plan view of a plurality of different replaceable medial wall parts.

Additional medial walls of varying angles or curves may be substituted for the adjustable medial walls 66 and 67. A set of medial walls is illustrated in FIG. 12, in which guidance angles of 10°, 15°, 20°, 25°, 30°, 35° and 40° are shown, for use on right or left condylar guidances 48 and 49, as may be desired. The angles depicted are not intended to be restrictive nor does their illustration preclude the use of curvatures in place of or in cooperation with such and different angles. Their configuration, except for the angles, is the same as for the previously described adjustable medial walls 66 and 67 and the means for attachment to the condylar guidance members 48 and 49 are thumbscrews, springs and washers like those designated 68, 83 and 84, respectively.

Figure 13:
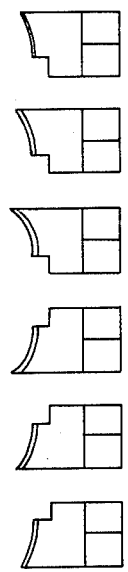
FIG. 13 is a top plan view of a plurality of different replaceable posterior wall parts.

Replaceable posterior walls of varying angles or curvatures may be substituted for the adjustable posterior walls 70 and 71, previously illustrated. In FIG. 13 is depicted a set of such posterior walls of various curvatures, all tangent to the posterior surface 78, for use on the right or left condylar guidances 48 and 49. Additional curvatures or angles may also be employed. The construction thereof, except for the posterior curvature or angulation, is like that of adjustable posterior wall 70 and their attachments to condylar guidances 48 and 49 are by thumbscrews, springs and washers like those designated 72, 87 and 88, respectively.

The dental articulator of this invention is preferably employed in conjunction with an earpiece facebow, such as that manufactured by Teledyne Hanau, a Teledyne Dental Company of Teledyne, Inc., and identified by catalogue number 159-1.

Although the facebow is not a part of the present invention it is employed in conjunction with the present articulator and therefore use of it and impression material carried on a metal or plastic (preferably metal) bite plate thereof for obtaining an occlusal imprint useful in transferring the patient's maxillary arch relationship to the present articulator, will be described herein.

The nylon earpieces of the earpiece facebow, sterilized before use, are placed in position for insertion into the external auditory meatus of the ears and the bite plate of the earpiece facebow is covered with a compound of choice to a suitable thickness for obtaining an occlusal imprint of the maxillary teeth. Then the softened impression material on the bite plate is seated against the maxillary teeth to create distinct cusp imprints without metal contact and with the stem of the bite plate extending approximately parallel to the sagittal plane. The impression material is then chilled while the bite plate is still being held firmly in position by the mandibular teeth. The imprint of the maxillary occlusal surface only will be used to transfer the maxillary cast to the articulator and therefore no attention needs to be given to the mandibular relation when making this registration. The facebow is then brought gently over the face with the stem of the bite plate entering the loose bite clamp and the nylon earpieces are positioned in the ears. The frame is then moved laterally so as symmetrically to adjust the scales, while maintaining a comfortable, yet secure suspension of the nylon earpieces in the meatus. Both frame thumbscrews are then tightened to maintain this symmetry and the clamp thumbscrew is securely tightened to lock the facebow in fixed relationship with the bite plate. The patient's intercondylar width is recorded from the symmetrically adjusted scales on the facebow. Thus, a 6.2 cm. reading on the right and left scales totals an intercondylar width of 12.4 cm. Then the two frame thumbscrews are released and the scales, with nylon earpieces, are withdrawn from the meatus. Next, the entire facebow assembly is removed from the patient, with care being exercised not to disturb the bite plate-bite clamp relationship.

Three interocclusal records of terminal relations are next made, one of a centric, one of a right lateral and one of a left lateral bite, each being made by a suitable method, according to the operator's preference, using methods and materials of choice.

The condyle thumbscrews and the right and left condyles are then positioned according to the previously recorded intercondylar width of the patient. Thus, a 12.4 cm. intercondylar width, being closest to the 12.0 width of the four widths shown, indicates that the condyles should be mounted in the bridge of the lower member with the stems thereof inserted in the holes designated 12.0. The condyle thumbscrews are threaded into the corresponding bridge holes and are tightened against the flats of the condyle stems to maintain desired vertical and transverse axial relationships. It has been found by experimentation that although the positive mounting means of the present invention does not exactly duplicate intercondylar widths the results of the use of the matching positive mounts for the condyles and their guidances are that the condyle and condylar wall relationships are more accurately maintained than when such positions are continuously variable over a range of widths without such settings being positive settings like those of the present mounting means. Thus, although such might not have been expected, the use of the present apparatus results in more accurate simulated condylar movements than does an "infinitely settable" (within a range) condylar width. In part this is due to the accumulation of errors in making the four settings and resulting lack of conformance of condyle and condylar wall positions for the continuous settings that are avoided by use of the present invention.

The intercondylar width of the right and left condylar guidance keystones or mounting means is set to the same width as the condyles and the corresponding intercondylar thumbscrews are tightened. Next the right and left posterior walls are adjusted to 0 position and the thumbscrews therefor are tightened, after which a similar operation is repeated with respect to the right and left medial walls except that they are adjusted to a 3 mm. position (three lines from 0). The horizontal inclinations of both condylar guidances, which regulate positions of the superior walls, are adjusted to 0° and the corresponding thumbscrews are tightened. Next, the incisal pin position is adjusted so that the registration groove thereof is aligned with the under side of the upper member and the thumbscrew therefor is tightened. A thin coating of petroleum jelly is applied to surfaces of the upper member which will subsequently be exposed to the stone mounting medium and a mounting plate is attached to the upper member.

In the next operation the facebow is mounted on the lower member of the articulator. First the mounting jig is tightly attached with the horizontal stud thereof extending forwardly and in line with the sagittal plane. The thumbscrew is loosened to lower the pivot. Nylon earpieces are removed, the frame thumbscrews are fully released and the scales are withdrawn from the frames, reversed in position and placed in the openings in the condyle compensator at the inside of the bow, after which the frame thumbscrews are engaged in the keyways. The facebow assembly thus produced is attached to the lower member of the articulator by equally adjusting the scales to securely suspend the condyle compensators over the transverse axis shafts or studs of the condyles, and the frame thumbscrews are tightened to maintain this symmetrical adjustment. The condyle compensators provide an average distance of 12 mm. from the patient's condyle center to the external auditory and meatus center. The interior position of the facebow assembly is then lowered to rest the aluminum frontal portion of the bite plate on the horizontal stud of the mounting jig. This aligns the incisal edge imprint of the upper centrals at a level with the average incisal reference notch in the incisal pin, 47 mm. below the condylar plane. The pivot is then raised to contact the under side of the bite plate and is locked in position by its thumbscrew to stabilize and carry the weight of a maxillary cast and stone mounting media for it.

To mount the maxillary cast such is first seated and luted into the occlusal imprint of the bite plane. Then the upper member of the articulator is placed onto the lower member with the condylar guidances or joint walls over their respective condyles. The articulator is locked into centric position by rotation of right and left centric locks or override mechanisms to engage with the annular grooves of the transverse axis shafts on the condyles and the thumbscrews are tightened. As was mentioned previously, such action restricts the articulator to opening and closing hinge movements only, devoid of any protrusive, vertical, lateral or immediate side shift displacements. The upper member of the articulator is then swung partially open and a mixture of stone is placed on the cast. The upper member is swung forward to embed the mounting plate and to bring the incisal pin into contact with the incisal cup. Mounting is completed with the use of a spatula, and excess material is removed to promote ease of removal and accurate reattachment of the cast to the upper member. Upon complete set of the stone mounting the maxillary cast is disengaged from the bite plate and the facebow and mounting jig are removed.

To mount the mandibular cast the articulator is first inverted and the mandibular cast is placed on the maxillary cast without the aid of a centric relation record. The position of the mandibular cast with respect to the articulator is measured and noted for further use. The centric relation record is then interposed and is luted to the maxillary and mandibular casts, following which the incisal pin is adjusted so that the dimension previously referred to would be the same as that previously determined when the centric relation record was not in place. Thus, on removal of the centric relation record and subsequent to the mounting of the mandibular cast the upper and lower members would be parallel. The lower member of the articulator is then swung back and a mixture of stone is placed on the mandibular cast, after which the lower member is swung over to embed the mounting plate into the stone and to bring the incisal pin into contact with the incisal cup. As in the mounting of the maxillary cast, the mounting is completed with the use of a spatula. Note that one must make certain that the condyles are locked in their centric position. Upon complete set of the mounting the articulator is placed in an upright position and the centric relation record is removed from between the casts.

The condylar guidances or condyle joint walls are adjusted after full disengagement of the right and left centric locks and after removal of the upper member of the articulator from the lower member. The right and left thumbscrews for the posterior walls, medial walls and the inclination of the condylar guidances are slightly loosened and the incisal pin is removed. Then the upper member is engaged with the lower member of the articulator and the right lateral interocclusal relation record between the maxillary and mandibular casts is accurately seated. The maxillary cast is grasped and it and the upper member in this right lateral relation record are immobilized, after which the left condylar guidance (balancing or non-working side) is rotated to contact the superior surface with the condyle and a left condylar thumbscrew is tightened. Adjustment is simplified if the articulator is placed on a hard and rigid workbench or work surface which acts as a sounding board and amplifies the "click" of the condyle as it contacts the superior surface of the condylar guidance or joint wall. The adjustment may also be made by sight and/or feel but it has been found that the "click" technique is generally superior. The left medial wall (balancing side) is slid outwardly to gently contact the condyle and the left medial thumbscrew is tightened, after which the right posterior wall (working side) is slid inwardly to gently contact the condyle and the right posterior thumbscrew is tightened. The right lateral record is removed and the left lateral interocclusal relation record is accurately seated between the maxillary and mandibular casts. The maxillary cast is grasped to immobilize it and the upper member in this left lateral relation record and the right condylar guidance (balancing side) is rotated to contact the superior surface with the condyle after which the right condylar thumbscrew is tightened. Then the right medial wall (balancing side) is slid outwardly to gently contact the condyle and the right medial thumbscrew is tightened, following which the left posterior wall (working side) is slid inwardly to gently contact the condyle and the left posterior thumbscrew is tightened. Then the left lateral interocclusal relation record may be removed.

What may be termed an incisal guide is prepared by a method which first involves carefully engaging the upper member of the articulator and bringing the casts into centric occlusion. An elastic band is then applied over the articulator to assure that the condyles maintain constant contact with the walls of the condylar guidance during any excursions from centric position and return to such position. The incisal pin is replaced and lowered into contact with the incisal cup, after which the incisal thumbscrew is tightened securely. The spherical end of the incisal pin (the bottom thereof) and the interior of the incisal cup are lubricated with a thin coating of petroleum jelly and the two retaining screws at the sides of the incisal cup are firmly attached to it. A 10 cm. × 10 cm. piece of 0.04 mm. thick polyvinyl chloride sheet material is placed between the maxillary and mandibular casts to resist abrasion of the stone cusps during fabrication of the incisal guide. A proprietary acrylic resin produce, sold under the name Hanau Pantacrylic, is mixed in a proportion of 2 milliliters of liquid to 5 grams of powder and is stirred with a spatula to a creamy consistency. The upper member of the articulator is raised and held elevated to permit filling the incisal cup with the acrylic resin mixture, which completely covers the two cup retaining screws. About five minutes after mixing, the upper member is lowered so that the incisal pin enters into the resin mix, at which time the mix is sufficiently thick so that it begins to retain its shape after distortion. Then various excursions should be made. The approved method for making the excursions includes gently guiding the maxillary cast into a full and straight protrusive movement by applying thumb pressure at the anterior of such cast and then promptly returning to centric position. From this centric position the maxillary cast should be gently guided into a full right lateral movement by thumb pressure at the right side of the cast to insure the Bennett shift and Bennett angle, after which return is made to the centric position. The maxillary cast is guided through a full left lateral excursion with its subsequent return to centric by a similar method. Firm pressure is applied to the left side of the cast so as to provide the full utilization of the condylar guidance settings. The incisal pin must never be used to make lateral excursions from centric as to do so will probably negate Bennett shift and Bennett angle, causing the working condyle to merely rotate.

It will be noted the the incisal pin displaces the acrylic resin and the three excursions mentioned should be repeated every fifteen seconds until the acrylic has set. It is expected that the working time for making the full set will be approximately eight minutes. Upon complete set of the acrylic polymeric material incisal guidance the frontal area of the plastic may be relieved or suitably cut away to permit free opening and closing of the upper member at a centric relation. The acrylic incisal guidance may be removed from the incisal cup, if desired, by removing the two acrylic retaining screws and prying it out of the cup. Alternatively a bottom plate (not shown) in the cup may be moved upwardly by turning a screw (not shown) threaded into the cup base and pushing toward a base disc or washer (not shown). The maxillary and mandibular casts may be removed from the articulator too, and by reproducing the various settings of the condyles, condylar guidances and incisal pin and by repositioning the acrylic incisal guide after reinstallation of the casts, the patient's maxillary and mandibular movements may be re-simulated.

After setting up of the articulator to simulate a patient's maxillary and manibular movements the dentist or dental technician may form and shape teeth and partial denture models in the stone or in wax or other material held in place in the articulator. The described apparatus is useful for working on both mandibular and maxillary teeth and gum sections and may be inverted for most convenient employment, in which position relative tooth movements may also be made and viewed. Due to the fact that the incisal rod height may be adjusted, grinding of cast tooth surfaces may be avoided. Although the present articulator is intended for employment in fabrication of fixed prostheses it may also be employed for making full and partial dentures. Additionally, the articulator may be useful as an educational and research tool.

An important advantage of the invented structure is in the removability of the upper member to facilitate working on or examination of the upper teeth. However, the primary advantages of the present articulator reside in the accuracy of the simulation of tooth and jaw movements and fittings, the reproducibility of settings of the articulator to re-simulate such previously established relationships, and the ease of operation thereof. Also important is the production of a smoother and more accurate movement of the balancing condyle (or condylar guidance) as the bearing surface shifts from posterior superior to medial. Previous shifts where both the posterior superior and medial surfaces were straight walled do not as accurately match the movement of the human condyle in its guidance.

To maintain the accuracy of simulation of jaw movements it is important that the condylar mounts, stems or pins and the mounts for the condylar guidance support accurately fit the openings into which such mounts are inserted. Normally such openings will be accurately positioned so that corresponding mounts are held within 0.00 to 0.1 mm., preferably 0.02 to 0.04 mm. of exact conformance. Also, for best fitting of the condyle with the condylar guidance walls the condyle will be spherical and the mounting stem will be cylindrical and cover less than 25% of the spherical area, e.g., 15% thereof. Preferably, the number of symmetrical positions for mounting of the condyles will be from 3 to 6 and most preferably will be 4. The intercondylar distances apart of the mount axes will usually be from 1 to 1.6 cm., preferably about 1.5 cm. and the range of intercondylar distances will be from 8 to 15 cm., preferably 9 to 13.5 cm. The extent of movement of each of the posterior and medial guidance walls will usually be from 0 to 5 mm., preferably 0 to 3 mm., usually marked at 1 mm. increments. The range of rotation of the mount and the superior guidance wall will usually be from 0 to 60°.

While various materials of construction may be employed for the present articulators it is preferred to utilize dimensionally stable materials such as metals, e.g., stainless steel, brass, bronze, steel and aluminum, although certain parts, preferably non-critical with respect to dimensions, may be made of synthetic organic polymeric materials, such as nylons, acrylics, fiberglass-reinforced polyesters, phenol formaldehydes, urea formaldehydes, polypropylenes, polystyrenes, epoxies and polyacetals, among others. Normally the metal parts will be die cast, forged or cast and machined, but other manufacturing methods may also be employed. Instead of acrylic materials for making the incisal guidance other moldable synthetic organic polymers are also useful, although usually not as good. Similarly, modifications may be made in the present structure which relate to non-critical aspects thereof. For example, the shapes of the various parts, the locations of set screws and the interfittings of elements thereof may be adjusted.

The invention has been described with respect to a preferred embodiment thereof but it is to be understood that it is not limited to such embodiment because one of skill in the art with the present specification and drawing before him will be able to utilize substitutes and equivalents without departing from the invention.

What is claimed is:

1. In a dental articulator for simulating relative jaw and tooth movements, an improvement which comprises a pair of simulated condyles on a lower mounting means, which lower mounting means simulates a part of a lower jaw, a pair of parts extending sidewardly and outwardly from near the locations of the condyles, a pair of movable mounting means for a simulated maxilla for movement thereof with respect to the condyles, condylar joint walls, bearable against the condyles, override means, and at least a partial peripheral channel in each of the said parts, in each of which an override means may be rotatably held against lateral movement, said override means including guide means for moving in the peripheral channel, when engaged, so that the articulator is in movable centric position, which guide means is removable from the channel to permit simulated forward and sideward maxillary movements.

2. In a dental articulator, the improvement according to claim 1 wherein each of the pair of matching parts is a shaft coaxial with the associated condyle, each shaft includes at least a partially peripheral channel in which the override means may be rotatably held against lateral movement and the override means includes arc-shaped guide means for rotating the simulated maxilla with respect to the shaft.

3. In a dental articulator, the improvement according to claim 2 wherein each of the pair of shafts includes a peripheral channel about the circumference thereof, in which channel the override means may be rotatably held by the channel walls against the lateral movement so that the articulator is in movable centric position.

4. In a dental articulator for simulating relative jaw and tooth movements, an improvement which comprises a pair of simulated condyles on a common axis, each condyle being selectively, positively and accurately spaceable apart from the other in any of at least three pre-set positions on a lower mounting means which simulates part of a lower jaw, a pair of matching shafts coaxial with the axis of the condyles, which shafts each extend sidewardly and outwardly from the condyles, a pair of movable mounting means for a simulated maxilla for movement thereof with respect to the condyles, each of said mounting means being selectively, positively and accurately spaceable apart in any of at least three pre-set positions so as to support means for simulating condylar joint walls, superior, posterior and medial wall means held to each of the mounting means for the simulated maxilla at each of the simulated condyles and bearable against the condyles, the superior wall means being vertically rotatable and the posterior and medial wall means being laterally movable to desired positions to simulate condylar joint walls and to control condylar movements and such superior, posterior and medial wall means being maintainable in such desired positions, and override means adjacent to each of the condyles and pivotally held to the superior wall means at each of the condyles, for selectively bearing against a portion of each of the shafts extending from such condyles to hold the articulator in movable centric position and for disengaging from such shaft to permit simulated forward and sideward jaw movements.

5. In a dental articulator, the improvement according to claim 4 wherein the rear portions of each of the superior wall means are of a shape having a vertically curved component so as to produce a smooth transitional relative movement of the condyle with respect to the condylar joint wall as the condyle moves from bearing against the posterior portion of the superior wall means to bearing against the medial wall means.

6. In a dental articulator for simulating relative jaw and tooth movements, an improvement which comprises a pair of simulated condyles on a common axis, each condyle being selectively, positively and accurately spaceable apart from the other in any of at least three pre-set positions on a lower mounting means which simulates part of a lower jaw, a pair of matching shafts coaxial with the axis of the condyles, which shafts each include a peripheral channel and extend sidewardly and outwardly from the condyles, a pair of movable mounting means for a simulated maxilla for movement thereof with respect to the condyles, each of said mounting means being selectively, positively and accurately spaceable apart in any of at least three pre-set positions so as to support means for simulating condylar joint walls, superior, posterior and medial wall means held to each of the mounting means for the simulated maxilla at each of the simulated condyles and bearable against the condyles, said superior, posterior and medial wall means being movable to desired positions to simulate condylar joint walls and to control condylar movements, and override means adjacent to each of the condyles, for selectively bearing against a portion of each of the shafts extending from such condyles in the peripheral channels thereof to hold the articulator against lateral movement and in rotatably movable centric position and for disengaging from such shaft to permit simulated forward and sideward jaw movements, said override means including arc-shaped guide means for rotating it with respect to the shaft, and the override means, superior, posterior and medial condylar joint wall means, mounting means and simulated maxilla being removable from the shafts and the condyles when the override means is in disengaged position.

7. In a dental articulator, the improvement according to claim 6 wherein the superior wall means are vertically rotatable, the posterior and medial wall means are laterally movable and all such means are maintainable in desired positions.

8. In a dental articulator, the improvement according to claim 7 wherein the simulated condyles are each spherical at upper surfaces thereof and for all except lower portions of lower surfaces thereof and are mounted at said lower portions on vertical mounts fitted to matching openings in the lower mounting means, the number of pre-set positions of each of the simulated condyles on the lower mounting means is from 4 to 6 and the distance between the adjacent positions for each of the simulated condyles is from 1 to 1.6 cm.

9. In a dental articulator, the improvement according to claim 8 wherein each of the mounting means for supporting means for simulating condylar joint walls is screw-mountable on a base portion, said base portion includes an exterior corner and said mounting portion includes a matching interior corner, with a mounting screw passing through any one of a plurality of openings in the mounting portion and being screwed into a threaded opening in the base portion so as to hold the simulated condylar joint walls in position about the condyle.

10. In a dental articulator for simulating relative jaw and tooth movements an improvement which comprises a pair of simulated condyles and separate superior, posterior and medial wall members for simulating such portions of such walls of condylar joints about each of the condyles, wherein the superior wall members are vertically rotatably adjustable in position, the medial and posterior wall members are laterally adjustable, and the superior wall members are each of a shape having a vertically curved component at rear sections thereof so that as a condyle is moved with respect to the condylar joint wall from bearing against the superior wall member to bearing against the medial wall member, a smooth transitional relative movement results.

11. In a dental articulator for simulating relative jaw and tooth movements, an improvement which comprises a pair of simulated condyles axially spaced apart on a lower mounting means which simulates a part of a lower jaw, a pair of matching shafts extending sidewardly and outwardly from the condyles, each of which shafts includes at least a partial peripheral channel, a pair of movable mounting means for a simulated maxilla for movement thereof with respect to the condyles, each of said mounting means being spaced apart so as to support means for simulating condylar joint walls, superior and medial wall means held to each of the mounting means for the simulated maxilla at each of the simulated condyles, and bearable against the condyles, said superior and medial wall means being movable to desired positions to simulate condylar joint walls and to control condylar movements, and override means adjacent to each of the condyles, for selectively bearing against a portion of each of the shafts extending from such condyles to hold the articulator in movable centric position and for disengaging from such shafts to permit simulated forward and sideward jaw movements, which override means are rotatable in the peripheral channels of the shafts to hold the simulated maxilla against lateral movement when in centric position and are disengageable from said channels to allow removal of the superior and medial condylar joint wall means, mounting means and simulated maxilla from the shafts and the condyles in such disengaged position.

12. In a dental articulator, the improvement according to claim 11 wherein the superior wall means are each of a shape having a curved component at a rear section thereof and the medial wall means are each adjustable and of a shape having a curved component so that, as the condyle is moved laterally relative to the condylar joint wall, such relative movement is in a smooth curve, a part of which is due to the condyle bearing against the superior wall member and the other part of which is due to the condyle bearing against the medial wall member, so that the relative movement is in a curve which simulates actual human condylar joint movement.

13. In a dental articulator for simulating relative jaw and tooth movements, an improvement which comprises a pair of simulated condyles axially spaced apart on a lower mounting means which simulates a part of a lower jaw, a pair of shafts extending sidewardly and outwardly from the condyles, each of which shafts includes at least a partial peripheral guide, a pair of movable mounting means for a simulated maxilla for movement thereof with respect to the condyles, each of said mounting means being spaced apart so as to support means for simulating condylar joint walls, superior and medial wall means held to each of the mounting means for the simulated maxilla at each of the simulated condyles, and bearable against the condyles, said superior and medial wall means being movable to desired positions to simulate condylar joint walls and to control condylar movements, and override means adjacent to each of the condyles, for selectively bearing against a portion of each of the shafts extending from such condyles to hold the articulator in movable centric position, and for disengaging from such shafts to permit simulated forward and sideward jaw movemets, which override means are rotatable with respect to the peripheral guides of the shafts to hold the simulated maxilla against lateral movement when in centric position and are disengageable from said guides to allow removal of the superior and medial condylar joint wall means, mounting means and simulated maxilla from the shafts and the condyles in such disengaged position.

14. In a dental articulator, the improvement according to claim 13 wherein the superior wall means are each of a shape having a curved component at a rear section thereof and the medial wall means are each adjustable and of a shape having a curved component so that, as the condyle is moved laterally relative to the condylar joint wall, such relative movement is in a smooth curve, a part of which is due to the condyle bearing against the superior wall member and another part of which is due to the condyle bearing against the medial wall member, so that the relative movement is in a curve which simulates actual human condylar joint movement.

* * * * *